(12) United States Patent
Hinago et al.

(10) Patent No.: US 8,106,238 B2
(45) Date of Patent: Jan. 31, 2012

(54) METHOD FOR PRODUCING GLYCOLIC ACID

(75) Inventors: Hidenori Hinago, Tokyo (JP); Hajime Nagahara, Tokyo (JP); Toshiya Aoki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 879 days.

(21) Appl. No.: 11/921,072

(22) PCT Filed: May 25, 2006

(86) PCT No.: PCT/JP2006/310426
§ 371 (c)(1),
(2), (4) Date: Apr. 17, 2008

(87) PCT Pub. No.: WO2006/126626
PCT Pub. Date: Nov. 30, 2006

(65) Prior Publication Data
US 2009/0118541 A1    May 7, 2009

(30) Foreign Application Priority Data
May 27, 2005 (JP) .................... 2005-154939

(51) Int. Cl.
*C07C 59/00* (2006.01)
(52) U.S. Cl. ........................................... 562/579
(58) Field of Classification Search .................. None
See application file for complete search history.

(56) References Cited

U.S. PATENT DOCUMENTS

| | | | |
|---|---|---|---|
| 2,153,064 A | 4/1939 | Larson | |
| 2,890,238 A * | 6/1959 | Sexton | 558/351 |
| 3,867,440 A * | 2/1975 | Kobetz et al. | 562/579 |
| 4,515,732 A | 5/1985 | Brazdil, Jr. et al. | |
| 4,634,789 A | 1/1987 | Teller et al. | |
| 2006/0160199 A1* | 7/2006 | DiCosimo et al. | 435/146 |

FOREIGN PATENT DOCUMENTS

| | | |
|---|---|---|
| EP | 0 426 394 A1 | 5/1991 |
| JP | 28-1074 B1 | 3/1953 |
| JP | 51-100027 A | 9/1976 |
| JP | 53-018015 B | 9/1976 |
| JP | 60-10016 B2 | 4/1978 |
| JP | 53-68725 A | 6/1978 |
| JP | 59-139341 A | 8/1984 |
| JP | 61-56086 A | 3/1986 |
| JP | 6-35420 B2 | 12/1986 |
| JP | 62-77349 A | 4/1987 |
| JP | 62-267257 A | 11/1987 |
| JP | 6-501268 A | 2/1994 |
| JP | 6-135923 A | 5/1994 |
| JP | 9-28390 A | 2/1997 |
| JP | 9-67300 A | 3/1997 |
| JP | 2004-43386 A | 2/2004 |
| JP | 2005-504506 A | 2/2005 |
| WO | WO-92/05138 A1 | 4/1992 |
| WO | WO-02/068658 A1 | 9/2002 |
| WO | 2006/069114 A2 | 6/2006 |
| WO | WO 2006/069110 A2 | 6/2006 |

OTHER PUBLICATIONS

Pentti, Salomaa. "The Kinetics of the Cannizzaro Reaction of Glyoxal," 1956, Acta Chemica Scandinavica, 10, pp. 311-319.
Yamamoto, Keizou, et al. "Purification and Characterization of Nitrilase Responsible for the Enantioselective Hydrolysis from *Acinetobacter* sp. AK 226," 1994, Agricultural and Biological Chemistry, vol. 55, No. 6, pp. 1459-1466.
Extended European Search Report dated May 7, 2010 for European Application No. 06766404.5.
Henry, "Sur Le Nitrile Glycolique et la Synthese Directe de L'acide Glycoliqiue," Bulletin De La Societe Chimique De France, 1890, p. 402, XP002579020.
Takahashi et al., Melt/Solid Polycondensation of Glycolic Acid to Obtain High-Molecular-Weight Poly(glycolic acid), Polymer, vol. 41, No. 24, Nov. 1, 2000, pp. 8725-8728, XP004228799.
Yamamoto et al., "Purification and Characterization of Nitrilase Responsible for the Enantioselective Hydrolysis from *Acinetobacter* sp. AK 226," Agric. Biol. Chem., vol. 55, No. 6, Jun. 1, 1991, pp. 1459-1466, XP000226135.
Chem. Ber. 54, 1392-1396 (1921).
Arrhenius et al., J. Org. Chem., vol. 62, pp. 5522-5525, Aug. 1997. "Glycolonitrile Oligomerization: Structure of Isolated Oxazolines, Potential Heterocycles on the Early Earth", XP55002979.
European Search Report dated Aug. 12, 2011 for European Application No. 11 16 2394.

* cited by examiner

*Primary Examiner* — Paul A Zucker
(74) *Attorney, Agent, or Firm* — Birch, Stewart, Kolasch & Birch, LLP

(57) ABSTRACT

Provided is a production method of glycolic acid having a first step of preparing glycolonitrile from formaldehyde and hydrocyanic acid and a second step of hydrolyzing the glycolonitrile into glycolic acid directly or via a glycolate salt, which method can produce glycolic acid in easy production and purification steps while consuming less energy. In the production method, by carrying out the first and second steps continuously or by storing the glycolonitrile obtained in the first step at pH 4 or less and carrying out a hydrolysis reaction of the second step at from pH 5 to 9, a production yield of glycolic acid, activity for the production of glycolic acid and accumulated concentration of glycolic acid are improved, resulting in the production of glycolic acid having an improved purity and quality.

6 Claims, 1 Drawing Sheet

METHOD FOR PRODUCING GLYCOLIC ACID

TECHNICAL FIELD

The present invention relates to glycolic acid useful as raw materials for polymerization, cosmetics, medicinal products, boiler compounds, cleaning agents, leather tanning agents, chelating agents of a metal ion and the like; and a production method of glycolic acid.

BACKGROUND ART

Glycolic acid has conventionally been used mainly as boiler compounds, cleaning agents, leather tanning agents, chelating agents of a metal ion and the like. In recent years, it expands its application to cosmetics and drugs for external use. Glycolic acid to be used as a drug for external use is desired to contain a lower level of harmful impurities. Glycolic acid has recently been expected also as a raw material for polyglycolic acid having biodegradability and a gas barrier function.

Typical examples of a conventionally known method for producing glycolic acid include (1) a method of reacting carbon monoxide, formaldehyde and water in the presence of a strongly acidic catalyst under high-temperature and high-pressure conditions, (2) a method of reacting chloroacetic acid with sodium hydroxide, (3) a method of carrying out a Cannizzaro reaction between glyoxal available by oxidation of ethylene glycol and a strong alkali to form a glycolate salt, and then adding an acid to liberate glycolic acid from the resulting glycolate salt; (4) a method of carrying out a liquid-phase reaction between glyoxal available by oxidation of ethylene glycol and water in the presence of an inorganic catalyst; (5) a method for catalytic oxidation of ethylene glycol in the presence of a noble metal catalyst and oxygen; and (6) a method of carrying out oxidative esterification of ethylene glycol with methanol and oxygen to obtain methyl glycolate and then hydrolyzing into glycolic acid.

The method of reacting carbon monoxide, formaldehyde and water in the presence of a strongly acidic catalyst under high-temperature and high-pressure conditions includes, for example, a method of reacting formaldehyde and carbon monoxide in an aqueous organic solvent in the presence of a hydrogen fluoride catalyst (refer to, for example, Patent Document 1) and a method of reacting formaldehyde and carbon monoxide in an aqueous medium in the presence of a sulfuric acid catalyst (refer to, for example, Patent Documents 2 and 3).

This method has a problem that glycolic acid must be produced by using special reaction equipment and special reaction conditions of high temperature and high pressure. In addition, it inevitably produces byproducts such as organic acids, for example, formic acid or methoxyacetic acid showing mutagenicity. Glycolic acid obtained using reaction conditions of high temperature and high pressure contains a large amount of various impurities such as methanol due to side reaction and sulfuric acid used as the catalyst. This method needs a large amount of labor and energy for removal of these impurities to purify the reaction product and is therefore inefficient. In addition, this method requires both an anion exchange resin and a cation exchange resin. Described specifically, the steps constituting this method are very complicated, because anion exchange resin, live steam stripping and cation exchange resin are necessary for the removal of sulfuric acid, low-boiling-point impurities, and metal impurities, respectively.

The method (2) of reacting monochloroacetic acid with sodium hydroxide (refer to, for example, Patent Documents 4 and 5) requires use of an about stoichiometric amount of sodium hydroxide. This leads to a problem that sodium chloride contaminated with an organic matter appears stoichiometrically as a waste material. Moreover, owing to sodium chloride generated stoichiometrically as a by-product raises the slurry concentration after concentration, leading to poor operability and a large loss. Another problem is that a salt is not removed completely and remains in the product.

A problem common to the methods (3) to (6) is that since ethylene glycol is produced using ethylene oxide as a raw material, a step of producing ethylene glycol is long and in addition, ethylene oxide which is explosive must be handled in the production process.

The production method of (3) is a method of carrying out a Cannizzaro reaction between glyoxal available by oxidation of ethylene glycol and a strong alkali to form a glycolate salt, and then adding an acid to liberate glycolic acid from the resulting glycolate salt (refer to, for example, Non-patent documents 1 and 2). The Cannizzaro reaction is a disproportionation reaction so that a large amount of byproducts is generated, which results in a deterioration in the productivity and formation of a large amount of impurities.

The production method (4) is a method of carrying out a liquid-phase reaction between glyoxal available by oxidation of ethylene glycol and water in the presence of an inorganic catalyst (refer to, for example, Patent Document 6). In this method, a component of the metal salt used as the catalyst is mixed in the solution obtained by the reaction so that a step of removal of it is necessary. A purification step for the removal of the metal salt component from the solution obtained by the reaction is industrially complex and difficult so that necessity of it is a great drawback of this method.

The production method (5) is a method for catalytic oxidation of ethylene glycol in the presence of a noble metal catalyst and oxygen (refer to, for example, Patent Document 7). This method has drawbacks such as inevitable use of a noble metal such as platinum which is expensive and is a scarce resource; poor productivity due to long reaction time; and generation of many kinds of byproducts because the selectivity to glycolic acid is low owing to the oxidation reaction.

The production method (6) is a method of carrying out oxidative esterification of ethylene glycol with methanol and oxygen to obtain methyl glycolate and then hydrolyzing into glycolic acid (refer to, for example, Patent Document 8). This method has drawbacks such as inevitable use of a noble metal such as gold which is expensive and is a scarce resource and generation of many kinds of byproducts because of a low selectivity to methyl glycolate in the oxidative esterification.

The conventional production methods have the above-described problems. In particular, glycolic acid obtained by these methods is insufficient as a monomer for polymerization into polyglycolic acid.

As a production method of glycolonitrile, a method of preparing glycolonitrile from formaldehyde and hydrocyanic acid (refer to, for example, Patent Documents 9 to 13) and an oxidation method of acetonitrile (refer to, for example, Patent Documents 14 and 15) are known. According to these known documents, glycolonitrile obtained from formaldehyde and hydrocyanic acid is used as a raw material for glycine or hydantoin.

A method of preparing ammonium glycolate by hydrolyzing glycolonitrile by using microorganisms in the presence of an aqueous solvent is also known (refer to, for example, Patent Documents 16 to 18). These documents however do not include a description on the production method of glycolonitrile.

This means that a method using hydrocyanic acid as a starting raw material is not known as a production method of glycolic acid.

Patent Document 1: Japanese Patent Laid-Open No. 59-139341
Patent Document 2: U.S. Pat. No. 2,153,064
Patent Document 3: International Patent Publication No. 6-501268
Patent Document 4: Japanese Patent Laid-Open No. 62-77349
Patent Document 5: Japanese Patent Laid-Open No. 9-67300
Non-patent Document 1 Chem. Ber. 54, 1395 (1921)
Non-patent Document 2: Acta Chem. Scand. 10, 311 (1956)
Patent Document 6: Japanese Patent Publication No. 6-35420
Patent Document 7: Japanese Patent Publication No. 60-10016
Patent Document 8: Japanese Patent Laid-Open No. 2004-43386
Patent Document 9: Japanese Patent Laid-Open No. 62-267257
Patent Document 10: Japanese Patent Laid-Open No. 53-68725
Patent Document 11: Japanese Patent Laid-Open No. 6-135923
Patent Document 12: Japanese Patent Publication No. 53-18015
Patent Document 13: Japanese Patent Laid-Open No. 51-100027
Patent Document 14: U.S. Pat. No. 4,634,789
Patent Document 15: U.S. Pat. No. 4,515,732
Patent Document 16: Published Japanese Translation of PCT International Publication No. 2005-504506
Patent Document 17: Japanese Patent Laid-Open No. 9-28390
Patent Document 18: Japanese Patent Laid-Open No. 61-56086

DISCLOSURE OF THE INVENTION

Problems to be Solved by the Invention

An object of the present invention is to provide a process which consumes less energy and has easy production and purification steps, more specifically, a production method of glycolic acid in which a production yield of glycolic acid, activity for the production of glycolic acid and accumulated concentration of glycolic acid are high and which can produce glycolic acid having an excellent quality and therefore suited as raw materials for polymerization, cosmetics, medicinal products, boiler compounds, cleaning agents, leather tanning agents and chelating agents of a metal ion, and also glycolic acid obtained using the above-described production method.

Means for Solving the Problems

The present inventors have proceeded with an extensive investigation in order to solve the above-described problem. As a result, it has been found that a production method of glycolic acid having a first step of obtaining glycolonitrile from formaldehyde and hydrocyanic acid and a second step of hydrolyzing the glycolonitrile into glycolic acid directly or hydrolyzing the glycolonitrile into a glycolate salt and then preparing glycolic acid therefrom consumes less energy and enables easy production and purification.

It has also been found that in the above-described production method having a first step and a second step, by performing the first and second steps continuously or by storing the glycolonitrile obtained in the first step at pH 4 or less and then carrying out the hydrolysis reaction of the second step at from pH 5 to 9, the production yield of glycolic acid, activity for the production of glycolic acid and accumulated concentration of glycolic acid can be improved and the glycolic acid thus obtained can have an improved impurity and also an improved quality as a raw material for polymerization, leading to the completion of the present invention.

In a first aspect of the present invention, there is thus provided a production method of glycolic acid, which comprises:
a first step of obtaining glycolonitrile from formaldehyde and hydrocyanic acid,
a second step of hydrolyzing the glycolonitrile into a glycolate salt,
a third step of preparing glycolic acid from the glycolate salt, wherein the first step and the second step are performed as a connected step.

In a second aspect of the present invention, there is also provided a production method of glycolic acid, which comprises:
a first step of obtaining glycolonitrile from formaldehyde and hydrocyanic acid, and
a second step of hydrolyzing the glycolonitrile into glycolic acid, wherein the first step and the second step are performed as a connected step.

In a third aspect of the present invention, there is also provided a production method of glycolic acid, which comprises:
a first step of obtaining glycolonitrile from formaldehyde and hydrocyanic acid,
a second step of hydrolyzing the glycolonitrile into a glycolate salt, and
a third step of preparing glycolic acid from the glycolate salt, wherein the glycolonitrile obtained in the first step is stored at pH 4 or less and the hydrolysis reaction of the second step is performed at a pH in the range of from 5 to 9.

In a fourth aspect of the present invention, there is also provided a production method of glycolic acid, which comprises:
a first step of obtaining glycolonitrile from formaldehyde and hydrocyanic acid, and
a second step of hydrolyzing the glycolonitrile into glycolic acid, wherein the glycolonitrile obtained in the first step is stored at pH 4 or less and the hydrolysis reaction of the second step is performed at a pH in the range of from 5 to 9.

ADVANTAGE OF THE INVENTION

According to the method of the present invention, glycolic acid can be produced while consuming less energy and employing easy production and purification steps.

In the method of the present invention, the activity for the production of glycolic acid, production yield of glycolic acid and accumulated concentration of glycolic acid are high and moreover the method enables production of glycolic acid having a high purity and excellent quality.

BEST MODE FOR CARRYING OUT THE INVENTION

Figure 1:
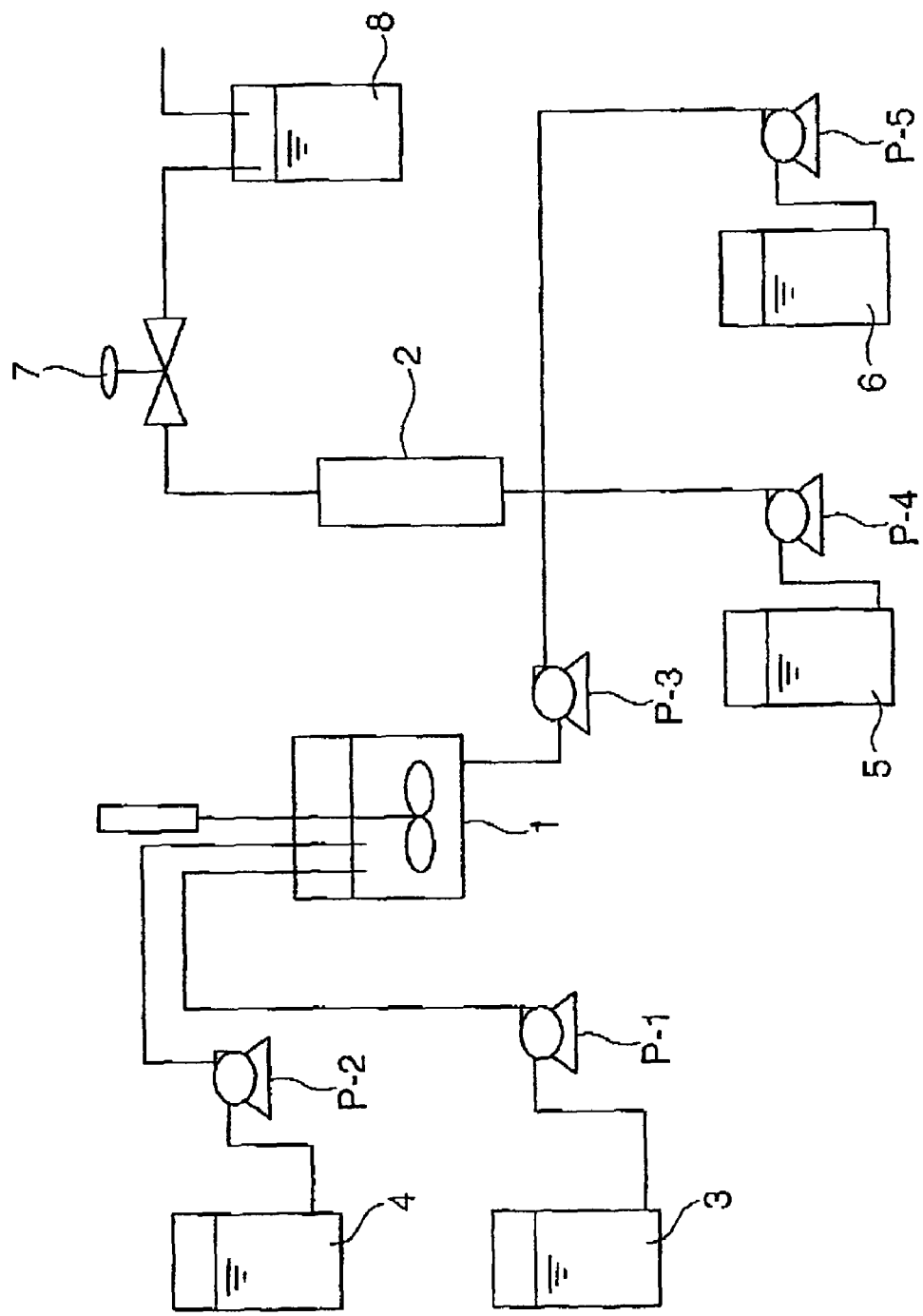
FIG. 1 is a schematic view illustrating one example of an apparatus for producing glycolic acid by using the method of the present invention.

The present invention will next be described specifically.

The first step will hereinafter be explained.

In the first step, for example, it is possible to make an aqueous formaldehyde solution absorb hydrocyanic acid in a hydrocyanic acid absorption tank employing a stirring tank flow system, or make pure water absorb hydrocyanic acid to prepare an aqueous hydrocyanic acid solution in the hydrocyanic acid absorption tank and then mix the resulting solution with an aqueous formaldehyde solution.

Formaldehyde and hydrocyanic acid are supplied at a formaldehyde to hydrocyanic acid (cyanhydric acid) molar ratio ranging preferably from 0.5 to 2, more preferably from 0.8 to 1.2, still more preferably from 0.95 to 1.05, especially preferably from 0.98 to 1.0.

A catalyst may be used in the reaction of the first step. As the catalyst, water soluble salts of an alkali metal can be used. Examples of the water soluble salts include hydroxides, halides, sulfites, acidic sulfites, sulfates, and formates of an alkali metal, of which hydroxides, sulfites and formates of an alkali metal are preferred, with sodium hydroxide and potassium hydroxide being more preferred. These catalysts may each be added as an aqueous solution, which has been prepared in advance, to hydrocyanic acid absorption water or the aqueous formaldehyde solution in the hydrocyanic acid absorption tank.

The amount of the catalyst, as a weight ratio of the metal to the amount of hydrocyanic acid, ranges preferably from 50 to 5000 ppm, more preferably from 100 to 600 ppm, still more preferably from 200 to 300 ppm.

Examples of the system of a reactor used for the synthesis reaction of glycolonitrile in the first step include stirring tank flow system and flow type tubular reaction system and combination thereof. Use of a stirring tank flow system as a first stage reactor and a flow type tubular reaction system as a second stage reactor is preferred.

In the stirring tank flow system, the reaction time is preferably from 10 to 300 minutes, more preferably from 10 to 50 minutes, still more preferably from 15 to 40 minutes, though depending on the amount of the catalyst and reaction temperature. In the flow type tubular reactor system, on the other hand, the reaction time is preferably from 10 to 300 minutes, more preferably from 10 to 50 minutes, still more preferably from 15 to 40 minutes.

The reaction temperature ranges preferably from 30 to 80° C., more preferably from 40 to 70° C., still more preferably from 45 to 60° C., though depending on the above-described amount of the catalyst and reaction time.

Operation pressure ranges preferably from 0 to 1.0 MPa/G, more preferably from 0.1 to 0.8 MPa/G (the term "/G" means a gauge pressure).

In the next place, the second step will be described.

Examples of the hydrolysis method in the second step include a method using a microbial enzyme having a hydrolytic activity of a nitrile group, a method using an acidic aqueous solution, and a method using an aqueous solution of an alkali metal. Of these, preferred is a method using a microbial enzyme having a hydrolytic activity of a nitrile group.

In the method using a microbial enzyme having a hydrolytic activity of a nitrile group, examples of the method using a microbial enzyme having a hydrolytic activity of a nitrile group include a method of adding the aqueous glycolonitrile solution obtained in the first step to an aqueous suspension of microorganisms or treated microorganisms (disrupted microorganisms, an enzyme isolated from disrupted microorganisms, immobilized microorganisms or a substance obtained by immobilizing an enzyme isolated and extracted from microorganisms), a method of adding the aqueous suspension of microorganisms or treated microorganisms to the aqueous glycolonitrile solution, and a method of immobilizing microorganisms or treated microorganisms in a known manner and then distributing the aqueous glycolonitrile solution thereto. By using the above-described method, it is possible to smoothly carry out a hydrolysis reaction of glycolonitrile and obtain glycolic acid.

The above-described microorganisms or treated microorganisms and glycolonitrile may be charged in reaction equipment to give concentrations of from 0.01 to 5 wt. % and from about 1 to 40 wt. %, respectively, each in terms of a dry weight of the microorganisms. The reaction may be carried out at a temperature of, for example, in the range of from 0 to 60° C., preferably from 10 to 50° C. for, for example, from 1 to 100 hours, preferably from 1 to 24 hours, more preferably from 4 to 15 hours.

It is also possible to start with a low concentration of glycolonitrile and add more over time or change the reaction temperature over time. For pH control, a buffer may be added prior to the reaction or an acid or alkali may be added during the reaction.

Examples of microorganisms suited as a microorganism for producing a microbial enzyme having a hydrolytic activity of a nitrile group include, but not limited to, microorganisms belonging to *Acinetobacter* sp., *Rhodococcus* sp., *Corynebacterium* sp., *Alcaligenes* sp., *Mycobacterium* sp., *Rhodopseudomonas* sp., and *Candida* sp.

The *Acinetobacter* sp. is preferred and a microbial enzyme produced by the *Acinetobacter* sp. has a considerably high hydrolytic activity.

Specific examples of it include following strains deposited by Asahi Kasei Chemicals (1-1-2, Yuraku-cho, Chiyoda-ku, Tokyo, Japan):

(1) *Acinetobacter* sp. AK226 strain of Deposit Number; FERM BP-08590 deposited on Jan. 7, 2004 (original deposit date) at International Patent Organism Depositary/National Institute of Advanced Industrial Science and Technology (AIST Tsukuba Central 6, 1-1, Higashi 1-chome, Tsukuba-shi, Ibaraki-ken 305-8566, Japan).

(2) *Acinetobacter* sp. AK227 strain of Deposit Number: FERM BP-08591 deposited on Jan. 7, 2004 (original deposit date) at International Patent Organism Depositary/National Institute of Advanced Industrial Science and Technology (AIST Tsukuba Central 6, 1-1, Higashi 1-chome, Tsukuba-shi, Ibaraki-ken 305-8566, Japan).

The microbial enzyme produced by microorganisms belonging to the *Acinetobacter* sp. is excellent because an average activity for the production of glycolic acid (=(weight of glycolic acid and glycolate salts prepared)/(dry weight of a cell×reaction time)) or accumulated concentration of glycolic acid (=concentration of glycolic acid in a reactor) is high and glycolic acid available using it has a high purity.

For the preparation of an aqueous solution of the glycolate salt by removing the microorganisms and high molecular impurities such as proteins derived therefrom from the mixture of the glycolate salt and microorganisms, centrifugal filtration, separation through a microfiltration membrane (MF) and separation through a ultrafiltration membrane (UF) may be employed either singly or in combination. The microorganisms which have been once filtered off can be used again.

In the method using an acidic aqueous solution, as the acidic aqueous solution, an aqueous sulfuric acid solution, an aqueous hydrochloric acid solution, an aqueous nitric acid solution, an aqueous phosphoric acid solution or an aqueous organic acid solution can be used, of which the aqueous sulfuric acid solution is preferred.

A molar ratio of the acid to glycolonitrile is preferably from 0.5 to 4, more preferably from 1 to 2, still more preferably from 1.05 to 1.5.

The reaction time is preferably from 0.1 to 200 hours, more preferably from 1 to 50 hours, still more preferably from 3 to 30 hours, though depending on a reaction temperature. The reaction temperature is preferably from 35 to 100° C., more preferably from 40 to 90° C., still more preferably from 50 to 80° C. The operation pressure is preferably from 0 to 1.0 MPa/G, more preferably from 0.1 to 0.8 MPa/G.

In the method using an aqueous solution of an alkali metal, as the aqueous solution of an alkali metal, an aqueous solution of sodium hydroxide, an aqueous solution of potassium hydroxide or an aqueous solution of lithium hydroxide can be used, of which the aqueous solution of potassium hydroxide and aqueous solution of sodium hydroxide are preferred.

The molar ratio of an alkali metal to glycolonitrile is preferably from 0.5 to 4, more preferably from 1 to 1.3, still more preferably from 1.05 to 1.5.

The reaction time is preferably from 0.1 to 50 hours, more preferably from 0.3 to 10 hours, still more preferably from 0.5 to 5 hours, though depending on a reaction temperature. The reaction temperature is preferably from 35 to 100° C., more preferably from 40 to 90° C., still more preferably from 50 to 80° C. The operation pressure is preferably from 0 to 1.0 MPa/G, more preferably from 0.1 to 0.8 MPa/G.

Examples of the reactor system used for the hydrolysis reaction include stirring tank flow system and flow type tubular reaction system, and combination thereof. Use of a stirring tank flow system as a first stage reactor and a flow type tubular reactor system as a second stage reactor is preferred.

The language "the first step and the second step are performed as a connected step" will next be explained.

In one mode of the present invention, the first step and the second step are performed as a connected step. The language "the first step and the second step are performed as a connected step" as used herein means that the period from completion of the glycolonitrile synthesis reaction to the starting of hydrolysis of the thus synthesized glycolonitrile in the second step is within 10 days.

Specific examples of the method for performing them as a connected step include a method of performing the first step and the second step as a continuous process; a method of storing the glycolonitrile obtained in the first step in a tank or the like temporarily and then subjecting it to the second step; and a combination of these methods.

The method of performing the first step and the second step without interruption is preferred.

The period from the completion of the glycolonitrile synthesis reaction to the starting of hydrolysis of the thus synthesized glycolonitrile in the second step is preferably within 5 days, more preferably within 1 day.

The period exceeding 10 days decreases a production yield of glycolic acid in the second or third step and moreover, adversely affects the quality of glycolic acid. In particular, it leads to deterioration of the quality such as production of a colored substance and deterioration in polymerizability.

During the period from the completion of the glycolonitrile synthesis reaction to the starting of hydrolysis of the thus synthesized glycolonitrile in the second step, the glycolonitrile is stored at preferably 30° C. or less, more preferably 20° C. or less, still more preferably 10° C. or less.

The language "by storing the glycolonitrile obtained in the first step at pH 4 or less and carrying out the hydrolysis reaction of the second step at from pH 5 to 9" will next be explained.

In another mode of the present invention, the glycolonitrile obtained in the first step is stored at pH 4 or less and hydrolysis reaction of the second step is carried out at a pH in the range of from 5 to 9. The hydrolysis reaction of the second step is carried out preferably at a pH in the range of from 6 to 8.

When the second and third steps are performed after the glycolonitrile obtained in the first step is stored for a long period of time, a production yield of glycolic acid decreases and moreover, the glycolic acid thus obtained has a deteriorated quality. By storing the glycolonitrile obtained in the first step at pH 4 or less and carrying out hydrolysis reaction of the second step at from pH 5 to 9, activity for the production of glycolic acid, production yield of glycolic acid and accumulated concentration of glycolic acid are improved and glycolic acid having a higher quality is available.

Activity for the production of glycolic acid is low when the glycolonitrile obtained in the first step is stored at pH 4 or less and the hydrolysis reaction of the second step is performed with the pH kept at pH 4 or less.

When the glycolonitrile obtained in the first step is stored at pH 4 or greater for 10 days or more and the hydrolysis reaction of the second step is performed at from pH 5 to 9, the production yield of glycolic acid decreases and the glycolic acid thus obtained has a drastically deteriorated quality.

The third step will next be explained.

The third step is necessary when the product in the second step is a glycolate salt. This step is often required when a method using a microbial enzyme having a hydrolytic activity of a nitrile group or a method using an aqueous solution of an alkali metal is employed as a hydrolysis method.

Examples of the method of the third step for producing glycolic acid from the glycolate salt include a method of bringing an aqueous solution of the glycolate salt into contact with a hydrogen-ion-loaded cation exchange resin, a method of converting the glycolate salt into the corresponding ester, separating the ester therefrom and then obtaining glycolic acid by hydrolysis, and a method of using electrodialysis. Electrodialysis is preferred because it generates only a small amount of waste products such as salts.

When the hydrogen-ion-loaded cation exchange resin is used, a weakly acidic cation exchange resin or a strongly acidic cation exchange resin can be used as the cation exchange resin. The cation exchange resin can be regenerated using sulfuric acid, hydrochloric acid, nitric acid or the like, of which sulfuric acid is preferred. When such resins are used for the first time, they are preferably pretreated and washed with water sufficiently in advance. The resins are pretreated by washing with an acid and a base alternately.

The time spent for the treatment with the cation exchange resin is, in the case of a batch system, preferably from 3 to 60 minutes, more preferably from 6 to 30 minutes. When the treatment is performed in a continuous system, the rate of feed into a resin tower is, in terms of a liquid space velocity ((L/Hr)/L−resin), preferably from 0.1 to 100, more preferably from 1 to 10.

The treatment temperature is preferably from 5 to 70° C., more preferably from 20 to 50° C.

The cation exchange resin after use can be regenerated by feeding an acid such as sulfuric acid into the cation exchange resin and then removing the acid remaining in the liquid by the aid of pure water.

For obtaining glycolic acid by converting the glycolate salt into its ester, isolating the ester and then hydrolyzing the ester into glycolic acid, a known method can be employed.

Examples of electrodialysis include two-cell electrodialysis using a bipolar membrane and an anion or cation exchange membrane and three-cell electrodialysis using a bipolar membrane, an anion exchange resin and a cation exchange resin.

As an electrode for an electrodialyzer, any known ones can be used without limitation. Examples of the anode include platinum, titanium/platinum, carbon, nickel, ruthenium/titanium, and iridium/titanium, while those of the cathode include iron, nickel, platinum, titanium/platinum, carbon and stainless steel.

As the bipolar membrane, any conventionally known bipolar membranes, that is, those having a cation exchange membrane and an anion exchange membrane adhered to each other, can be used without particular limitation. A cation exchange group of the cation exchange membrane constituting the bipolar membrane is not particularly limited and groups such as sulfonic acid group and carboxylic acid group can be used, with the sulfonic acid group being preferred. An anion exchange group of the anion exchange membrane is also not particular limited and ion exchange groups such as ammonium salt group, pyridinium salt group, primary amino group, secondary amino group and tertiary amino group can be used, with the ammonium salt group being preferred.

As the cation exchange membrane, known ones can be used without particular limitation and those having a sulfonic acid group, a carboxylic acid group, or a mixture of a plurality of these ion exchange groups can be used.

As the anion exchange resin, known ones also can be used without particular limitation and those having an ion exchange group such as ammonium salt group, pyridinium salt group, primary amino group, secondary amino group or tertiary amino group, or a mixture of a plurality of these ion exchange groups can be used.

The temperature upon electrodialysis ranges preferably from 5 to 70° C., more preferably from 20 to 50° C. A current density is not particularly limited, but is preferably from 0.1 to 100 A/cm$^2$, more preferably from 2 to 20 A/cm$^2$. With regard to the distance between ion exchange membranes, they may be placed at a commonly employed distance, preferably from 0.01 to 10 mm, more preferably from 0.05 to 1.50 mm.

Raw materials employed in the present invention will next be described.

The formaldehyde which is a raw material used for the reaction of the present invention can be supplied usually as formalin.

Hydrocyanic acid, which is a raw material used for the reaction of the present invention, can be supplied in any form such as gas, liquid or aqueous solution. Industrially produced hydrocyanic acid typically contains sulfur dioxide, acetic acid and the like as a stabilizer. In addition, it contains acrylonitrile as an impurity.

In the production method of glycolic acid according to the present invention, hydrocyanic acid having a content of each of additives and impurity not greater than 5000 ppm is preferred, with that having the content not greater than 2000 ppm being more preferred.

The acrylonitrile content is preferably 500 ppm or less, more preferably 200 ppm or less, still more preferably 50 ppm or less.

The acetic acid content is preferably 2000 ppm or less, more preferably 1000 ppm or less, still more preferably 500 ppm or less. The acetic acid content is, on the other hand, preferably 50 ppm or greater.

The sulfur dioxide content is preferably 2000 ppm or less, more preferably 1000 ppm or less, still more preferably 500 ppm or less. The sulfur dioxide content is, on the other hand, preferably 50 ppm or greater.

The total content of sulfur dioxide, acetic acid and acrylonitrile is preferably 5000 ppm or less, more preferably 2000 ppm or less, still more preferably 1000 ppm or less, especially preferably 500 ppm or less.

Glycolic acid yielded using the above-described raw materials and method can be used as a product as is, but can also be purified using, either singly or in combination, separation through a microfiltration (MF) membrane, an ultrafiltration membrane (UF), an adsorbent such as active charcoal and an anion exchange resin. Following that, water is evaporated from the glycolic acid thus obtained to provide it as a concentrated product.

The glycolic acid thus obtained (or aqueous solution of glycolic acid) can be used as raw materials for polymerization, cosmetics, pharmaceuticals, anti-incrustants, detergents, leather tanning agents, or chelating agents of a metal ion and the like. It is particularly suited as raw materials for polymerization. The language "raw material for polymerization" means a raw material which is polymerized as is, a raw material for the preparation of glycolide, a raw material for preparation of glycolide via an oligomer or the like, in short, it can be used finally as a polymerized product. The polymerization may be either homopolymerization or copolymerization with a compound, such as lactic acid, having, in the molecule thereof, a hydroxyl group and a carboxyl group.

EXAMPLES

For the hydrolysis of glycolonitrile in the second step of Examples and Comparative Examples, *Acinetobacter* sp. AK226 strain (which will hereinafter be called "AK226", simply) was used. AK226 was deposited on Jan. 7, 2000 at International Patent Organism Depositary/National Institute of Advanced Industrial Science and Technology (1-1, Higashi 1-chome, Tsukuba-shi, Ibaraki-ken, Japan) and has a deposit number FERM BP-08590.

The AK 226 strain was cultured under the following conditions. A medium was prepared by dissolving, in distilled water, fumaric acid, meat extract, peptone, sodium chloride, ε-caprolactam, potassium dihydrogen phosphate, magnesium sulfate heptahydrate, ammonium chloride, ferric sulfate heptahydrate, manganese chloride tetrahydrate and cobalt chloride hexahydrate to give concentrations of 1.0 wt. %, 1.0 wt. %, 1.0 wt. %, 0.1 wt. %, 0.3 wt. %, 0.2 wt. %, 0.02 wt. %, 0.1 wt., 0.003 wt. %, 0.002 wt. %, and 0.002 wt. %, respectively. The medium had a pH of 7.5. The strain was cultured at 30° C. for one day.

Example 1

<First Step>

A glycol acid synthesis reaction was performed in reaction equipment as illustrated in FIG. 1.

In a first step, glycolonitrile is synthesized in Reactors 1 and 2. In Reactor 1, hydrocyanic acid is converted into an aqueous solution thereof, while in Reactor 2, cyanhydrin reaction is carried out to generate glycolonitrile. Reactor 1 is a jacketed stainless-steel autoclave having an inner volume of 200 mL and equipped with a stirrer. Reactor 1 was fed with Pure water 3 at a rate of feed of 56.2 (g/hr) by Pump P-1 and Hydrocyanic acid 4 at a rate of feed of 44.4 (g/hr) by Pump P-2, whereby an aqueous solution of hydrocyanic acid was obtained. Hydrocyanic acid employed here had a purity of 99.5 wt. % and contained 600 ppm of acetic acid, 300 ppm or sulfur dioxide and 2000 ppm of acrylonitrile as impurities. The temperature of Reactor 1 was set at 17° C.

Reactor 2 is a jacketed coiled-pipe-type reactor having an inner volume of 120 mL and warm water of 47° C. was circulated through the jacket. The aqueous solution of hydrocyanic acid obtained in Reactor 1 was sent to Reactor 2 by Pump P-3. Pump 3 works so as to keep a holdup amount at 60 mL while actuating a liquid-level gauge.

Reactor 2 was fed with 37.1 wt. % Aqueous formaldehyde solution 5 (Special reagent grade, product of Wako Pure Chemicals) by Pump P-4 at rate of feed of 132.4 (g/hr) and 0.05 wt. % Aqueous sodium hydroxide solution 6 by Pump P-5 at rate of feed of 44.4 (g/hr) and the aqueous hydrocyanic acid solution, Aqueous formaldehyde solution 5 and Aqueous sodium hydroxide solution 5 were mixed at the inlet of Reactor 2. Reactor 2 had, at the outlet thereof, Back pressure valve 7 by which the pressure in the system was maintained at 0.5 MPa/G. The retention time in Reactor 2 was 26 minutes. A solution obtained during latter 30 minutes of the feeding, which was performed for 1 hour, was sampled, whereby 138 g of Aqueous glycolonitrile solution 8 was obtained. As a result of analysis by gas chromatography, it was found that the resulting aqueous solution had a glycolonitrile content of 33.5 wt. % and the yield of glycolonitrile was 99.5%.

<Second Step>

A suspension containing 18.0 wt. %, in terms of dry weight, of microorganisms of AK 226 was prepared in advance by collecting them from the culture medium by centrifugation, washing three times with distilled water, and adding distilled water to the washed microorganisms. The suspension (6 g) of the microorganisms was charged in a 400-ml glass autoclave purged with a nitrogen gas and a mixture of 100 g of the 33.5 wt. % aqueous glycolonitrile solution obtained in the first step and 100 g of distilled water was fed to the autoclave in 5 hours. The reaction was carried out at pH 7 and a reaction temperature of 40° C. The feeding in the second step was started about 30 minutes after the aqueous glycolonitrile solution was obtained in the first step. After reaction for 12 hours (5 hours for feeding and 7 hours after completion of the feeding), refrigerated centrifugation was performed at 10,000 rpm for 15 minutes to isolate the microorganisms and the supernatant was collected. Microorganisms and proteins remaining in the supernatant were removed by a ultrafiltration membrane under pressure to obtain a reaction solution.

<Third Step>

Pure water was passed through a resin tower filled with 1000 ml of "Amberlite IRC-76 (H type) (provided by Organo Co. Ltd.), a weakly acidic cation exchange resin, followed by passing of an aqueous solution obtained by diluting 100 g of the reaction solution obtained in the second step with 100 g of pure water and then passing of 2000 g of pure water, each through the resin tower. An aqueous solution of glycolic acid was then collected. The above-described operation was performed at a temperature of 25° C. and a volume passing rate of 2.5 (L/Hr). The liquid space velocity was calculated to be 2.5 ((L/Hr)/L-resin).

As a result of analysis by high performance liquid chromatography ("Shimadzu LC-10", column: "Shodex RSPak KC-811", UV detector (wavelength: 210 nm), eluent: a 0.75% aqueous phosphoric acid solution, rate of feed of the eluent: 1 ml/min, analysis time: 90 minutes), the glycolic add was obtained in a yield of 99% based on the glycolonitrile, had a quality indicator (=sum of peak areas other than glycolic acid)/peak area of glycolic acid)) of 0.007 and was not colored.

Example 2

A glycolic acid was prepared in a similar manner to Example 1 except that the aqueous solution of glycolonitrile obtained in the first step was fed in the second step one day after preparation of the aqueous solution. The glycolic acid was obtained in a yield of 99% based on glycolonitrile, had a quality indicator of 0.008 and was not colored.

Example 3

A glycolic acid was prepared in a similar manner to Example 1 except that the aqueous solution of glycolonitrile obtained in the first step was fed in the second step three days after preparation of the aqueous solution. The glycolic acid was obtained in a yield of 98% based on glycolonitrile, had a quality indicator of 0.013 and was not colored.

Example 4

A glycolic acid was prepared in a similar manner to Example 1 except that the aqueous solution of glycolonitrile obtained in the first step was fed in the second step after it was cooled to −10° C. and stored for 7 days. The glycolic acid was obtained in a yield of 99% based on glycolonitrile, had a quality indicator of 0.010 and was not colored.

Example 5

A glycolic acid was prepared in a similar manner to Example 1 except that the aqueous solution of glycolonitrile obtained in the first step was stored for 3 months at a pH changed to 3 with sulfuric acid and then sodium hydroxide was added to the aqueous glycolonitrile solution thus stored to change its pH to 7. The glycolic acid was obtained in a yield of 99% based on glycolonitrile, had a quality indicator of 0.007 and was not colored.

Comparative Example 1

A glycolic acid was prepared in a similar manner to Example 1 except that the aqueous glycolonitrile solution obtained in the first step was fed in the second step three months after preparation of the aqueous glycolonitrile solution.

The glycolic acid was obtained in a yield of 10% based on glycolonitrile and was colored remarkably.

Comparative Example 2

A glycolic acid was prepared in a similar manner to Example 1 except that the aqueous solution of glycolonitrile obtained in the first step was stored for 3 months at a pH changed to 3 with sulfuric acid and then the aqueous glycolonitrile solution thus stored was used as was. A conversion ratio of glycolonitrile to glycolic acid was 5%, suggesting that hydrolysis of glycolonitrile hardly occurred.

INDUSTRIAL APPLICABILITY

The present invention provides a method of producing glycolic acid comprising easy production and purification steps and capable of producing it while consuming less energy. According to the production method of the present invention, a production yield of glycolic acid, activity for the production of glycolic acid, and accumulated concentration of glycolic acid are high and the glycolic acid thus produced has an excellent quality. The glycolic acid obtained by the production method of the present invention is useful as raw materials for polymerization, cosmetics, medicinal products, boiler compounds, cleaning agents, leather tanning agents, chelating agents of a metal ion and the like.

The invention claimed is:

1. A production method of glycolic acid, which comprises:
    a first step of obtaining a solution of glycolonitrile from formaldehyde and hydrocyanic acid,
    a second step of treating the glycolonitrile solution of the first step so that the glycolonitrile is hydrolyzed into a glycolate salt, and
    a third step of obtaining glycolic acid from the glycolate salt, wherein the first step and the second step are performed as a connected step.

2. A production method of glycolic acid, which comprises:
    a first step of obtaining a solution of glycolonitrile from formaldehyde and hydrocyanic acid,
    a second step of treating the glycolonitrile solution of the first step so that the glycolonitrile is hydrolyzed into a glycolate salt, and
    a third step of obtaining glycolic acid from the glycolate salt, wherein the glycolonitrile obtained in the first step is stored at pH 4 or less and the hydrolysis reaction of the second step is performed at a pH in the range of from 5 to 9.

3. A production method of glycolic acid according to claims 1 or 2, wherein a microbial enzyme having a hydrolytic activity of a nitrile group is used for the hydrolysis reaction of the glycolonitrile.

4. A production method of glycolic acid according to claim 3, wherein the microbial enzyme is produced by *Acinetobacter* sp.

5. A production method of glycolic acid according to claim 4, wherein the hydrocyanic acid has a content of each of acrylonitrile, acetic acid and sulfur dioxide not greater than 5000 ppm.

6. A production method of glycolic acid, which comprises:
    a step of preparing a mixed solution of formaldehyde and hydrocyanic acid;
    a step of preparing a reaction liquid by
    (a) adding a suspension liquid of microorganisms having a hydrolytic activity of a nitrile group to the mixed solution, or
    (b) storing the mixed solution at pH 4 or less and then hydrolyzing the mixed solution prepared in step (a) at a pH in the range of from 5 to 9; and
    a step of obtaining glycolic acid by conducting an ion exchange with the reaction liquid.

* * * * *